United States Patent [19]

Singleton

[11] Patent Number: 4,503,279

[45] Date of Patent: Mar. 5, 1985

[54] ETHYLENE OLIGOMERIZATION PROCESS

[75] Inventor: David M. Singleton, Seabrook, Tex.

[73] Assignee: Shell Oil Company, Houston, Tex.

[21] Appl. No.: 619,250

[22] Filed: Jun. 11, 1984

Related U.S. Application Data

[62] Division of Ser. No. 501,581, Jun. 6, 1983, Pat. No. 4,472,522.

[51] Int. Cl.$^3$ .............................................. C07C 2/02
[52] U.S. Cl. .................................. 585/523; 585/514; 585/525; 585/527
[58] Field of Search ................ 585/514, 523, 525, 527

[56] References Cited

U.S. PATENT DOCUMENTS 3,825,615  7/1974  Lutz .................................. 585/527
4,260,844  4/1981  O'Donnell et al. ................ 585/525

*Primary Examiner*—Curtis R. Davis

[57] ABSTRACT

Ethylene is oligomerized to linear, alpha-olefins by reacting ethylene in liquid phase solution in the presence of a catalyst composition produced by contacting in the presence of ethylene (1) a simple divalent nickel salt, (2) a boron hydride reducing agent, and (3) an o-dihydrocarbylphosphinophenyl alcohol or lower alkyl ether.

8 Claims, No Drawings

ETHYLENE OLIGOMERIZATION PROCESS

This is a division of application Ser. No. 501,581, filed June 6, 1983, now U.S. Pat. No. 4,472,522.

FIELD OF THE INVENTION

This invention relates to a process for the oligomerization of ethylene to a mixture of olefinic products having high linearity by using a catalyst comprising (a) a simple divalent metal nickel salt, (b) a boron hydride reducing agent and (c) an o-dihydrocarbylphosphinophenyl alcohol or lower alkyl ether.

BACKGROUND OF THE INVENTION

The present invention relates to the production of a mixture of olefinic products which are substantially alpha-olefins and which have a high degree of linearity. Such olefins comprise for example, those of the plasticizer range, i.e., $C_4$–$C_{10}$, those of the detergent range, i.e., $C_{12}$–$C_{20}$, and higher olefins, e.g., polyethylene. The lower molecular weight olefins can be converted to sulfonates or alcohols by known commercial processes. The $C_{12}$–$C_{20}$ olefins find use in the detergent-products area. Lower molecular weight alcohols can be esterified with polyhydric acids, e.g., phthalic acid to form plasticizers or polyvinylchloride.

U.S. Pat. No. 3,676,523, issued July 11, 1972, discloses the use of an ethylene oligomerization catalyst which comprises (1) a divalent nickel salt, (2) a boron hydride reducing agent, and (3) an o-dihydrocarbylphosphinobenzoic acid or alkali metal salt thereof. The use of a dihydrocarbylphosphinophenyl alcohol or lower alkyl ether rather than a dihydrocarbylphosphinobenzoic acid provides an entirely new class of ligands to be utilized with a catalyst for the oligomerization of ethylene. The phenol ligand is not subjected to decarboxylation during reaction processes as is the benzoic acid ligand. The phenol ligand also provides a different olefin distribution than the benzoic acid ligand, thus allowing for the production of alpha-olefins having a different carbon number distribution than those produced using the benzoic acid ligand.

SUMMARY OF THE INVENTION

The instant invention comprises a process for oligomerizing ethylene to a mixture of olefinic products comprising a large proportion of alpha-olefins having high linearity by reacting ethylene in liquid phase solution in the presence of a catalyst composition produced by contacting in a polar organic solvent in the presence of ethylene (1) a simple divalent nickel salt, (2) a boron hydride reducing agent, and (3) an o-dihydrocarbylphosphinophenyl alcohol or lower alkyl ether ligand. The process is characterized by ethylene conversion to an alpha-olefin product mixture wherein said alpha-olefins have a high degree of linearity.

DESCRIPTION OF THE PREFERRED EMBODIMENTS

Nickel Salts: In general, any simple divalent nickel salt can be employed for preparing the catalyst composition of the invention provided the nickel salt is sufficiently soluble in the reaction medium. By the term "simple divalent" nickel salt is meant a nickel atom having a formal valence of +2 and bonded through ionic or electrovalent linkages to two singly charged anionic groups (e.g., halides) or to one doubly charged anionic group (e.g., carbonate) and not complexed with or coordinated to any other additional molecular or ionic species. Simple divalent nickel salts therefore do not encompass complex divalent nickel salts which are bonded to one or two anionic groups and additionally complexed or coordinated to neutral chelating ligands or groups such as carbon monoxide and phosphines. However, simple divalent nickel salts are meant to include nickel salts containing water of crystallization in addition to one or two anionic groups.

In most instances, a simple divalent nickel salt with a solubility in the reaction diluent or solvent employed for catalyst preparation of at least 0.001 mole per liter (0.001M) is satisfactory for use as the nickel catalyst precursor. A solubility in the reaction diluent or solvent of at least 0.01 mole per liter (0.01M) is preferred, and a solubility of at least 0.05 mole per liter (0.05M) is most preferred. Reaction diluents and solvents suitably employed for catalyst preparation are the polar organic solvent suitably employed for the oligomerization process which solvents are defined below.

Suitable simple divalent nickel salts include inorganic as well as organic divalent nickel salts. Illustrative inorganic nickel salts are nickel halides such as nickel chloride, nickel bromide and nickel iodide, nickel carbonate, nickel chlorate, nickel ferrocyanide, and nickel nitrate. Illustrative organic divalent nickel salts are nickel salts of carboxylic acids such as nickel alkanoates of up to ten carbon atoms, preferably of up to six carbon atoms, e.g. nickel formate, nickel acetate, nickel propionate, nickel hexanoate and the like; nickel oxalate; nickel benzoate and nickel naphthenate. Other suitable organic salts include nickel benzenesulfonate, nickel citrate, nickel dimethylglyoxime and nickel acetylacetonate.

Nickel halides, especially nickel chloride, and nickel alkanoates, in part because of their availability at low cost and solubility in polar organic solvents are preferred nickel salts.

Dihydrocarbylphosphinophenol alcohol or lower alkyl ether: The o-dihydrocarbylphosphinophenyl alcohol or lower alkyl ether ligands employed in the preparation of the catalyst composition of the invention generally have from eight to 30 carbon atoms, but preferably from 14 to 20 carbon atoms, and are represented by the formula (1):

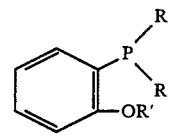

wherein R is a monovalent hydrocarbyl group and R' is hydrogen or lower alkyl of carbon number 1 to about 6.

Illustrative of suitable R groups are hydrocarbon alkyl R groups such as methyl, ethyl, isobutyl, lauryl, stearyl, cyclohexyl, and cyclopentyl; hydrocarbon alkyl or alkenyl R groups having aromatic substituents such as benzyl, phenylcyclohexyl and phenylbutenyl and aromatic R groups such as phenyl, tolyl, xylyl and p-ethylphenyl. Preferred R groups are alicyclic or aromatic groups of six to ten carbon atoms, especially phenyl and cycloalkyl of five to ten carbon atoms, especially cyclohexyl.

Illustrative o-dihydrocarbylphosphinophenol ligands of formula (1) are o-diphenylphosphinophenol, o-(methylphenylphosphino)phenol, o-(ethyltolylphosphino)- phenol, o-dicyclohexylphosphinophenol, o-(cyclohexylphenylphosphino)phenol and o-dipentylphosphinophenol.

Preferred phenol ligands of formula (1) are those wherein the R groups are aromatic or cycloalkyl of six to ten carbon atoms, particularly diarylphosphinophenols and arylcycloalkylphosphinophenols. Such aryl- and cycloaklyl-substituted phosphinophenol ligands are preferred largely because catalyst compositions prepared therefrom catalyze the oligomerization of ethylene to a product mixture containing a high proportion of oligomers in the useful $C_4$–$C_{10}$ and $C_{12}$–$C_{20}$ carbon ranges.

A most preferred ligand is o-diphenylphosphinophenol. This ligand can be prepared by methods readily available in the art. For example, see Rauchfuss, *Inorganic Chemistry*, volume 16, number 11, pp. 2966–2968, 1977.

Illustrative of suitable ether compounds would be the lower alkyl ether analogs of the phenol compounds described above, such as, for example, o-dihydrocarbylphosphinophenylmethyl ether, o-dihydrocarbylphosphinophenylethyl ether, o-dihydrocarbylphosphinophenylpropyl ether and the like. The lower alkyl moiety of the ether has a carbon number ranging from 1 to about 6. The methyl moiety is a preferred lower alkyl species. The most preferred ether ligand is o-diphenylphosphinophenylmethyl ether.

The exact form the ether ligand takes in forming a complex with nickel is not known. It is possible that the lower alkyl ether complex is converted in part into the alcohol complex under reaction conditions. It has been noted that for platinum complexes of o-diphenylphosphinophenylmethyl ether ligand, heating to about 270° C. caused dimethylation and formation of the phenol complex (C. E. Jones, B. L. Shaw and B. L. Turtle; J. Chem. Soc., Dalton Trans. (1974) 992).

When preparing the catalyst, the molar ratio of nickel salt to phenol/ether ligand is at least 1.1, i.e., at least one mole nickel salt is provided for each mole of phenol/ether ligand. Suitable molar ratios of nickel salt to phenol/ether ligand range from 1:1 to 5:1, although molar ratios of about 1.5:1 to 3:1 are preferred.

Boron Hydride Reducing Agent: In general, any boron hydride salt reducing agent of reasonable purity is suitable for use in the process of the invention. Specific examples include alkali metal borohydrides such as sodium borohydride, potassium borohydride and lithium borohydride; alkali metal alkoxyborohydrides wherein each alkoxy has one to four carbon atoms, such as sodium trimethoxyborohydride and potassium tripropoxyborohydride and tetraalkylammonium borohydrides wherein each alkyl has one to four carbon atoms, such as tetraethylammonium borohydride. Largely because of commercial availability, alkali metal borohydrides are preferred and especially preferred is sodium borohydride.

When preparing the catalyst, the molar ratio of boron hydride salt to nickel salt is at least 1:1. There does not appear to be a definite upper limit on the boron hydride/nickel ratio, but for economic reasons it is especially preferred that the molar ratio be not greater than 15:1. The preferred molar ratio of boron hydride to nickel salt is usually between about 1:1 and about 10:1. Best results are often obtained when the molar ratio is about 2:1.

Catalyst Preparation: The catalyst composition of the present invention is suitably preformed by contacting the catalyst precursors, i.e., the nickel salt, the phenol/ether ligands and the boron hydride reducing agent, in the presence of ethylene in a polar organic diluent or solvent, e.g., polar organic diluents or solvents employed for the oligomerization process which are not reduced by the boron hydride reducing agent. In a preferred modification, the solvent, the nickel salt and the phenol/ether ligand are contacted in the presence of ethylene before the addition of the boron hydride reducing agent. In order to obtain the improved catalyst of the invention, however, it is essential that the catalyst composition is prepared in the presence of the ethylene reactant. Generally, the catalyst precursors are contacted under 10 to 1,500 psig of ethylene.

By any modification, the catalyst is generally prepared at temperatures of about 0° C. to 50° C., although substantially ambient temperatures, e.g. 10° C. to 30° C., are preferred. Contact times of about 5 minutes to 1 hour are generally satisfactory.

Reaction Conditions: The ethylene is contacted with the catalyst composition in the liquid phase in the presence of a reaction solvent or diluent or solvent of up to about 30 liters per mole of ethylene are satisfactorily employed. Generally, the concentration of the catalyst, calculated as nickel metal, in the solvent or diluent is at least 0.001M, but preferably from about 0.1M to 0.5M.

Suitable solvents or diluents are non-polar organic solvents such as aliphatic hydrocarbons, e.g., alkanes, including cycloalkanes of from 5 to 20 carbon atoms, such as cyclopentane, cyclohexane, isohexane, heptane, isoctane, decane and eicosane; halo-alkanes, e.g., ethylene dichloride, hexachloroethane, 1,4-dichlorobutane; halocyclo-alkanes, e.g., chlorocyclohexane; aromatic compounds such as benzene, toluene and xylene; and haloaromatics such as chlorobenzene and hexafluorobenzene.

Other suitable solvents or diluents are polar organic compounds such as organic compounds containing atoms such as oxygen, sulfur, nitrogen and phosphorus incorporated in functional groups such as hydroxy, alkoxy, aryloxy, carbalkoxy, alkanoyloxy, cyano, amino, alkylamino, dialkylamine, amide, N-alkylamide, N,N-dialkylamide, sulfonylalkyl and like functional groups. Illustrative oxygenated organic solvents are fully esterified polyacyl esters of polyhydroxy alkanes such as glycerol triacetate, tetracyl esters of erythritol, diethylene glycol diacetate; monoesters such as ethyl acetate, butyl propionate and phenyl acetate; cycloalkyl ethers, e.g., dioxane, tetrahydropyran; acyclic alkyl ethers, e.g., dimethoxyethane, diethylene glycol dimethyl ether and dibutyl ether, aromatic ethers such as anisole, 1,4-dimethoxybenzene and p-methoxytoluene; aliphatic alcohols such as methanol trifluoroethanol, hexafluoroethanol, trifluoropropanol, sec-butanol, perfluorobutanol, octanol, dodecanol, cycloalkanols, e.g., cyclopentanol, and cyclo-hexanol, polyhydric acyclic hydroxyalkanes such as glycerol and trimethylene glycol, alkanediols of two to ten carbon atoms such as ethylene glycol, propylene glycol, 1,4-butanediol and 2,5-hexanediol; phenols, such as cresol, p-chlorophenol, m-bromophenol, 2,6-dimethylphenol, p-methoxyphenol, 2,4-dichlorophenol; and alkylene carbonates such as ethylene carbonate, propylene carbonate and butylene carbonate. Illustrative nitrogen-containing organic solvents are nitriles, e.g., acetonitrile and propionitrile; amines, e.g., butylamine, dibutylamine, trihexylamine, N-methylpyrolidine, N-methylpiperidine, and aniline; N,N-dialkylamides, e.g., N,N-dimethylformamide and N,N-dimethylacetamide. Illustrative sulfur-containing solvents are sulfolane and dimethylsulfoxide and illustrative phosphorus-containing solvents are trialkylphosphate, e.g., trimethylphsphate, triethylphosphate and tributylphosphate and hexaalkylphosphoramides such as hexamethylphosphoramide.

Preferred reaction diluents and solvents are polar organic solvents, particularly oxygenated organic solvents. Especially preferred are alkanediols of four to six carbon atoms, e.g., 1,4-butanediol and 2,5-hexanediol.

Polar organic solvents and diluents are preferred for use in the process in part because the ethylene oligomerization product mixture is essentially insoluble in such solvents and diluents. For example, when a polar organic solvent such as an alkanediol is employed, a two phase reaction mixture is formed, i.e., one phase comprising the ethylene oligomerization product mixture, i.e., the alpha-olefins, and a second phase comprising the nickel catalyst and the reaction diluent of solvent. Where a two phase reaction is formed, the ethylene oligomerization product phase is separated and the catalyst containing diluent or solvent phase is utilized for further ethylene oligomerization. Polar organic solvents are also preferred in part because the same solvents are employed in catalyst preparation as defined above.

The precise method of establishing ethylene/catalyst contact during the oligomerization reaction is not critical. In one modification, the catalyst composition and the solvent are charged to an autoclave or similar pressure reactor, the ethylene is introduced, and the reaction mixture is maintained with agitation at reaction temperature and pressure for the desired reaction period. In the modification wherein a polar organic solvent is employed and a two phase reaction is formed, ethylene is passed in a continuous manner into a reaction zone containing the catalyst composition and the diluent while ethylene oligomerization product mixture which is produced is concomitantly withdrawn from the reaction zone.

By any modification, the oligomerization process is conducted at moderate temperatures and pressures. Suitable reaction temperatures vary from about 50° C. to 90° C. The reaction is conducted at or above atmosphere pressure. The precise pressure is not critical so long as the reaction mixture is maintained substantially in a liquid phase. Typical pressures vary from about 10 psig to 5,000 psig with the range from about 400 psig to 1,500 psig being preferred.

The oligomerization products are separated and recovered from the reaction mixture by conventional methods such as fractional distillation, selective extraction, adsorption and the like. The reaction solvent, catalyst and any unreacted ethylene are recycled for further utilization. Spent catalyst, i.e., catalyst no longer active for ethylene oligomerization is regenerated by reacting with additional boron hydride reducing agent and nickel salt in the molar ratios (based on phenol/ether ligand) hereinbefore defined. No additional phenol/ether ligand is required to regenerate the spent catalyst.

During the oligomerization process ethylene is converted to dimer, trimer, tetramer, and like oligomers as well as polymers, i.e., polyethylene. The oligomer products are characterized by a high proportion (greater than about 70%) of linear terminal olefins with high linearity (greater than about 70%) and the polyethylene products are characterized by high linearity (greater than about 70%) and crystallinity. The particular product composition generally depends upon the catalyst employed, the solvent employed, the reaction conditions, particularly reaction temperatures and diluent and whether the catalyst is used in the homogeneous or heterogeneous state. These conditions can readily be determined by one skilled in the art.

The ethylene oligomer products are materials of established utility and many are chemicals of commerce. The products are converted by conventional catalysts to the corresponding alcohols. Alternatively the product olefins are converted to secondary alcohols by sulfuric acid-catalyzed hydration.

The instant invention will be illustrated by the following illustrative embodiments which are provided for illustration only and are not to be construed as limiting the invention.

ILLUSTRATIVE EMBODIMENTS

The following illustrative embodiments illustrate the typical preparation of the catalyst and its use of the process of the instant invention.

Dimethylacetamide solvent was charged to an autoclave in a dry box (30 ml). The autoclave was then attached to a manifold and flushed with nitrogen while 2.5 ml. of a solution of 0.24 g. $NiCl_2.6H_2O$ in 10 ml. of dimethylacetamide solvent was added, with stirring. This was followed by 10 ml. of a solution of 0.35 g. of ortho-diphenylphosphinophenol in 50 ml. of the dimethylacetamide solvent. The autoclave was closed and pressured with ethylene to 50 psig. (0.1 g) and the mixture was stirred for 20 minutes, after which the pressure had dropped to 35 psig. The autoclave was depressured and opened and 1.25 ml. of a solution of sodium borohydride in dimethylacetamide (0.19 g in 10 ml) was quickly added. Total amount present: $NaBH_4$ 0.126 mmoles; ortho-diphenylphosphinophenol 0.137 mmoles; $NiCl_2.6H_2O$ 0.252 mmoles. The autoclave was quickly reclosed, and pressured with ethylene to a pressure of about 300 psig. The vessel was stirred at room temperature for 20 minutes then was raised to a reaction temperature of about 90° C. After about 3 hours the reaction mixture was cooled and the products analyzed. The results are shown in Table 1. The conversion (mole %) on the basis of the feed was 81%, and the conversion on the basis of oligomer produced was 39%. The difference is presumed to be attributable to higher oligomer (polymer) production.

TABLE 1

| Product | PRODUCT OLIGOMERS | | | |
|---|---|---|---|---|
| | % Selectivity | % Linearity | % α-olefins | $K^{(a)}$ |
| $C_4$ | 2.5 | 100 | 97 | 1.94 |
| $C_6$ | 7.2 | 100 | 100 | 1.21 |
| $C_8$ | 11.5 | 100 | 92 | 0.86 |
| $C_{10}$ | 12.4 | 100 | 94 | 0.83 |
| $C_{12}$ | 12.3 | 100 | 96 | 0.79 |
| $C_{14}$ | 11.3 | 100 | 99 | 0.85 |
| $C_{16}$ | 11.0 | 100 | 95 | 0.81 |
| $C_{18}$ | 10.0 | 100 | 95 | 0.77 |
| $C_{20}$ | 8.6 | — | — | 0.78 |
| $C_{22}$ | 7.4 | — | — | 0.72 |
| $C_{24}$ | 5.7 | — | — | — |

$(a) K = \dfrac{C_{n+2}}{C_n}$

A sample of polymer removed from the reaction of the experiment described above was analyzed and determined to be polyethylene with the following characteristics.

By Differential Scanning Calorimetry:

| m.p. | 115.5° C. | (heating scan) |
|---|---|---|
| | 101.7° C. | (cooling scan) |
| | 112.0° C. | (reheat scan) |

By Gel Permeation Chromatography:

| Mn (number average molecular wt) | = 813 |
|---|---|
| Mw (weight average molecular wt) molecular weight distribution | = 1600 Bimodal |
| $M_Z$ (Z average) | = 4520 |
| Ō | = 1.98 |

The above process was repeated using methanol as a solvent. The reaction was run for 16 hours and the results are shown in Table 2. The conversion on the basis of the feed was 88% and the conversion on the basis of oligomer produced was 6.5%.

TABLE 2

OLIGOMER PRODUCTS

| Product | % Selectivity | % Linearity | % α-olefins | $K^{(a)}$ |
|---|---|---|---|---|
| $C_6$ | 10 | 100 | 100 | 1.38 |
| $C_8$ | 18.4 | 100 | 100 | 0.75 |
| $C_{10}$ | 17.2 | 100 | 100 | 0.73 |
| $C_{12}$ | 15.1 | 100 | 100 | 0.71 |
| $C_{14}$ | 12.5 | 100 | 100 | 0.72 |
| $C_{16}$ | 10.3 | 100 | 100 | 0.66 |
| $C_{18}$ | 7.7 | 100 | 100 | 0.65 |
| $C_{20}$ | 5.6 | 100 | 100 | 0.65 |
| $C_{22}$ | 3.3 | 100 | 100 | 0.54 |

Note - $C_4$ was obscured by solvent peak.

$^{(a)} K = \dfrac{C_{n+2}}{C_n}$

I claim:

1. A process of oligomerizing ethylene to a mixture of olefinic products comprising a large proportion of alpha-olefins having high linearity which process comprises reacting ethylene in liquid phase solution at a temperature of about 25° C. to 150° C. in the presence of a catalyst composition produced by contacting in a polar organic solvent in the presence of ethylene (1) a simple divalent nickel salt having a solubility of at least 0.001 mole per liter in said polar organic solvent (2) a boron hydride reducing agent and (3) an o-dihydrocarbylphosphinophenyl alcohol and/or lower alkyl ether ligand, the molar ratio of nickel salt to ligand being from about 1:1 to 5:1.

2. The process of claim 1 wherein the catalyst composition is produced in the presence of about 10 psig to 1500 psig of ethylene at a temperature of about 0° C. to 50° C. and the nickel salt has a solubility of at least 0.01 mole per liter in said polar organic solvent.

3. The process of claim 2 wherein the ethylene oligomerization reaction is conducted in the same polar organic solvent employed for catalyst preparation.

4. The process of claim 3 wherein the boron hydride reducing agent is an alkali metal borohydride and the molar ratio of alkali metal borohydride to nickel salt is about 1:1 to 10:1.

5. The process of claim 4 wherein the ligand is an o-diarylphosphinophenol.

6. The process of claim 5 wherein the nickel salt is a nickel halide.

7. The process of claim 6 wherein the polar organic solvent is an alkanediol of four to six carbon atoms.

8. The process of claim 7 wherein the nickel halide is nickel chloride, the ligand is o-diphenylphosphinophenol, the boron hydride reducing agent is sodium borohydride and the polar organic solvent is 1,4-butanediol.

* * * * *